US008969098B2

(12) United States Patent
Kaminski (10) Patent No.: US 8,969,098 B2
(45) Date of Patent: Mar. 3, 2015

(54) METHODS AND SYSTEMS PROVIDING REAGENT MIXING (75) Inventor: Edward Stephen Kaminski, North East, MD (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 129 days.

(21) Appl. No.: 13/636,944

(22) PCT Filed: Apr. 5, 2011

(86) PCT No.: PCT/US2011/031271
§ 371 (c)(1),
(2), (4) Date: Sep. 24, 2012

(65) Prior Publication Data
US 2013/0017621 A1    Jan. 17, 2013

Related U.S. Application Data (60) Provisional application No. 61/322,068, filed on Apr. 8, 2010.

(51) Int. Cl.
G01N 35/10 (2006.01)
B01F 11/00 (2006.01)
G01N 35/00 (2006.01)

(52) U.S. Cl.
CPC ............ *G01N 35/10* (2013.01); *B01F 11/0074* (2013.01); *G01N 2035/00544* (2013.01); *G01N 2035/1058* (2013.01)

USPC ............................................. 436/180

(58) Field of Classification Search
CPC .................................................. B01F 11/0074
USPC ............................................. 436/180
See application file for complete search history.

(56) References Cited

U.S. PATENT DOCUMENTS

| 4,984,475 A * | 1/1991 | Uffenheimer et al. ..... 73/864.22 |
| 6,418,800 B1 | 7/2002 | Mathur et al. |
| 2003/0207464 A1 | 11/2003 | Lemmo et al. |
| 2005/0014284 A1 * | 1/2005 | Jacobs et al. ............... 436/180 |
| 2007/0155019 A1 * | 7/2007 | Johnson et al. ............ 436/180 |

* cited by examiner

Primary Examiner — Christopher A. Hixson
Assistant Examiner — Emily Berkeley
(74) Attorney, Agent, or Firm — Dugan & Dugan, PC (57) ABSTRACT Disclosed are methods and systems adapted to provide mixing of a liquid reagent in an automated clinical analyzer. The methods include aspirating an air separator (e.g., an air slug) into the interior of a probe. A relatively small volume of reagent liquid is also aspirated into the probe adjacent to the air separator; the volume of liquid reagent being entirely contained within the probe. The volume of liquid reagent may be repeatedly aspirated and dispensed at a relatively high frequency to accomplish reagent mixing in the reagent container. Improved sample and reagent mixing may be promoted using a similar method. Systems carrying out the methods are provided, as are other aspects.

16 Claims, 8 Drawing Sheets

METHODS AND SYSTEMS PROVIDING REAGENT MIXING

RELATED APPLICATIONS

This application claims priority to U.S. Provisional Application Ser. No. 61/322,068 entitled "Improved Method of Mixing Sample/Reagent" filed on Apr. 8, 2010, the disclosure of which is hereby incorporated by reference in its entirety herein.

FIELD OF THE INVENTION

The present invention relates generally to methods and systems adapted to mix reagent in a clinical analyzer.

BACKGROUND OF THE INVENTION

Handling of liquid samples, reagents, and possibly other process fluids is essential for the implementation of automated clinical chemistry test methods. Conventionally, liquid samples, process fluids (e.g., purified water), and liquid reagents are aspirated and dispensed within an automated clinical analyzer by using a probe. In certain clinical analyzer instruments used to test for the presence of an analyte or other component in a biological fluid sample (otherwise referred to as "specimens"), it may be desirable to precisely meter one or more liquid reagents in the process. For example, in some automated testing systems (e.g., clinical analyzer instruments), a portion of a specimen contained in a sample container (such as a test tube, sample cup, vial, and the like) may be aspirated into a reaction vessel (e.g., a cuvette) in order to determine a presence of a particular analyte or component substance contained therein. As part of this process, precise metering of one or more liquid reagents into the reaction vessel along with the specimen portion may be accomplished. It is desired that during the metering process, the liquid reagent and the sample be mixed in order to provide a homogeneous mixture. In some testing methods, other process fluid (e.g., purified water) may also be added.

A conventional probe configuration used for aspiration includes a probe having a relatively small outer diameter. The probe may be coupled to a section of tubing that is, in turn, coupled to a pump (e.g., a piston pump). The aspiration system, including the probe and the pump, is typically primed with purified water.

Liquid reagents are often contained in a reagent container having a plurality of compartments. Some liquid reagents may include particles contained within a carrying liquid, and such particulates may settle over time. Accordingly, a mixing process onboard the automated clinical analyzer may be used to re-suspend these settled particulates into a homogeneous suspension of particles before they are aspirated and dispensed into a reaction vessel. Conventional mixing methods include (1) ultrasonic mixing and (2) aspiration and dispensing of a relatively large volume of the liquid reagent. Undesirably, the ultrasonic mixing method may cause damage to certain particulate reagents. Moreover, a prior art aspiration and dispense method (also referred to as the "sip-and-spit method") includes aspirating into the probe and the tube a relatively large volume of reagent (e.g., about 50% or more of the volume of the liquid reagent) from a particular reagent container and then dispensing the liquid reagent back into the particular reagent container one time. Such sip-and-spit methods may be inefficient at promoting or maintaining mixing of the particulate with the reagent carrier liquid, and may cause other problems.

Accordingly, methods and systems that may improve mixing of liquid reagent including particulates are desired.

SUMMARY OF THE INVENTION

According to a first method aspect, an improved method of providing a liquid reagent in an automated clinical analyzer is provided. The method includes aspirating a gas slug into a probe, aspirating a reagent slug into the probe from a reagent container, the reagent slug being contained entirely within an interior of the probe, and dispensing the reagent slug back into the reagent container.

In another method aspect, an improved method of mixing a biological fluid sample in an automated clinical analyzer is provided. The method includes dispensing a volume of the biological fluid sample into a reaction vessel; providing a rinsing liquid in the probe; aspirating a gas slug into the probe; aspirating a reagent slug into the probe wherein the reagent slug is separated from the volume of rinsing liquid by the gas slug; dispensing the reagent slug into the reaction vessel along with the biological fluid sample; and mixing the combination of reagent slug and biological fluid sample by repeatedly aspirating the combination into the probe followed by dispensing the combination back into the reaction vessel.

In a system aspect, an aspiration and dispensing system is provided. The system includes a probe including a probe interior; a reagent container; and an aspirator/dispenser coupled to the probe by a length of tubing, the aspirator/dispenser adapted to aspirate a gas slug into the probe interior following by aspiration of a reagent slug from the reagent container, wherein the reagent is repeatedly dispensed from, and re-aspirated into, the reagent container to accomplish mixing of reagent in the reagent container.

Still other aspects, features, and advantages of the present invention may be readily apparent from the following detailed description by illustrating a number of exemplary embodiments and implementations, including the best mode contemplated for carrying out the present invention. The present invention may also be capable of other and different embodiments, and its several details may be modified in various respects, all without departing from the spirit and scope of the present invention. Accordingly, the drawings and descriptions are to be regarded as illustrative in nature, and not as restrictive. The drawings are not necessarily drawn to scale. The invention is to cover all modifications, equivalents, and alternatives falling within the spirit and scope of the invention.

DETAILED DESCRIPTION

For at least the above-described reasons, achieving improved mixing of a process fluid, especially a liquid reagent including particulates, in medical specimen testing is desirable. It has been discovered by the inventor herein that the aspiration of a large volume of liquid reagent by the prior art sip-and-spit method causes the liquid reagent to travel a significant distance up into the tubing coupled to the probe, which may cause reagent wetting of the inside of the tubing, as witnessed by discoloration of the inner walls of the tubing. Wetting is the ability of a liquid to maintain contact with a solid surface, resulting from intermolecular interactions when the two are brought together.

Such reagent wetting may result in reagent carryover. Reagent carryover is where portions of the reagent liquid (or particulates) from a previous aspiration/dispense cycle will remain within the tubing and are then carried over into a subsequent aspiration/dispense cycle. Reagent carryover might possibly affect the accuracy of subsequent testing. Moreover, liquid reagent loss due to adherence/wetting to the interior surface of the tubing and probe might also affect current testing. Additionally, the inventor has recognized that, in some instances, there may be dilution of the liquid reagent from residual water wetting of an interior wall surface of the tubing and probe (e.g., water wetting) from when the system was previously primed with water.

Additionally, the inventor has recognized that, in conventional sip-and-spit methods, aspiration of such a relatively-large volume of liquid reagent requires a relatively-low pump speed. This low speed produces a relatively low fluid flow rate to help ensure that the reagent remains intact during the aspiration. In other words, if the pump is operated too rapidly, the relatively large volume of aspirated reagent may separate and develop undesirable internal air bubbles, etc. Accordingly, there remains a need for an improved aspiration/dispense method that does not damage particle reagents and that minimizes the aforementioned reagent carryover, reagent dilution, and/or loss of reagent volume. Furthermore, the affects that cause reagent carryover may also provide carryover of sample and/or or other process fluid.

In view of the foregoing problems, the present invention, in one aspect, provides methods and systems adapted to provide improved liquid reagent mixing. The improved mixing is accomplished according to the invention by aspirating a relatively small reagent slug in the probe, and then cycling the slug in rapid succession into and out of the reagent container at a relatively high frequency. This same rapid cycling may be used to mix the liquid reagent into a biological fluid sample.

These and other aspects and features of the invention will be described with reference to FIGS. 1-8 herein.

Figure 1:
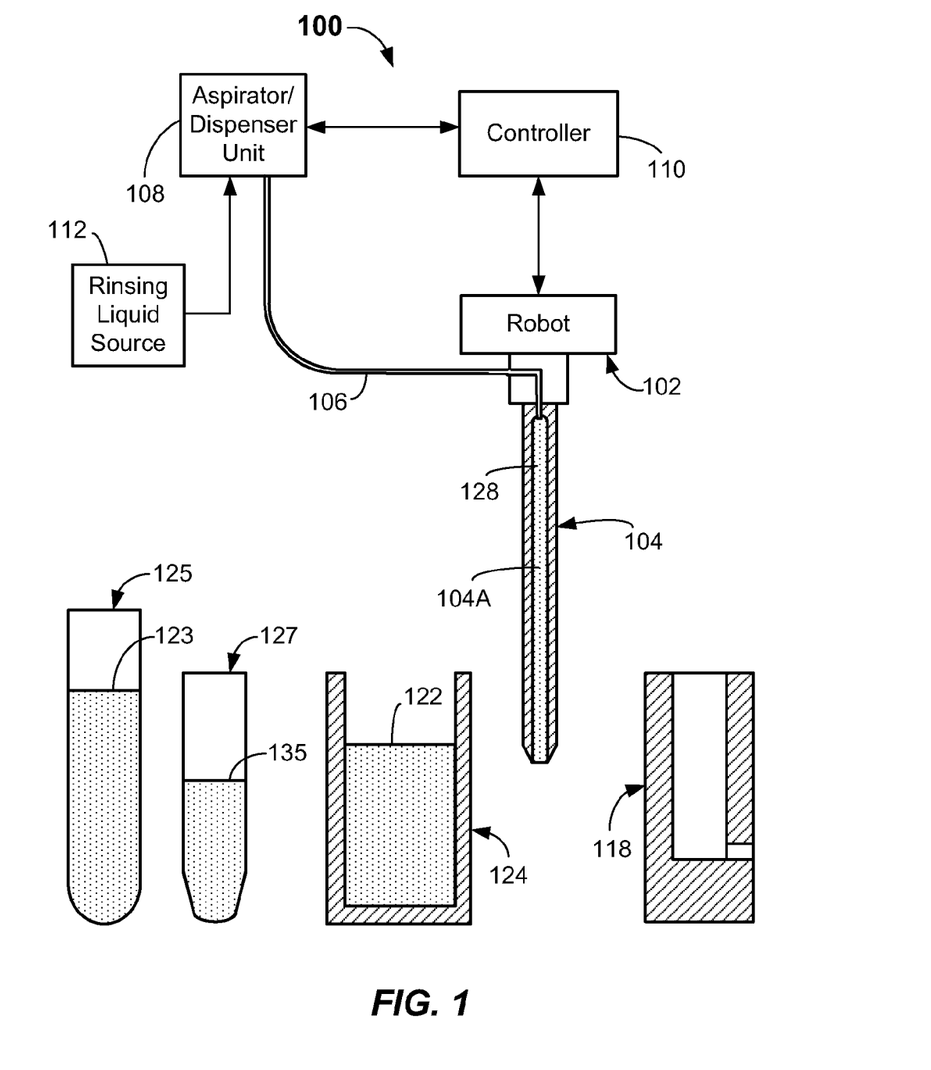
FIG. 1 is a partially cross-sectioned side view of an exemplary aspiration and dispensing system adapted to carry out methods according to an aspect of the present invention.

As represented in FIG. 1, a configuration of an aspiration and dispensing system 100 of the present invention is shown. The aspiration and dispensing system 100 includes a robot 102 having a probe 104 coupled thereto. The probe 104 may be a slender conventional probe having a probe interior 104A.

The robot 102 may be any suitable robot adapted to move the probe 104 to and from defined process locations. A section of tubing 106 is fluidly coupled to the interior 104A of the probe 104 and that tubing 106 is, in turn, fluidly coupled to an aspirator/dispenser unit 108. The robot 102 and aspirator/dispenser unit 108 may be operated by control signals from a controller 110 to aspirate and/or dispense fluids such as liquid reagent, rinsing liquid (e.g., purified water), and/or biological fluid sample.

Figure 2:
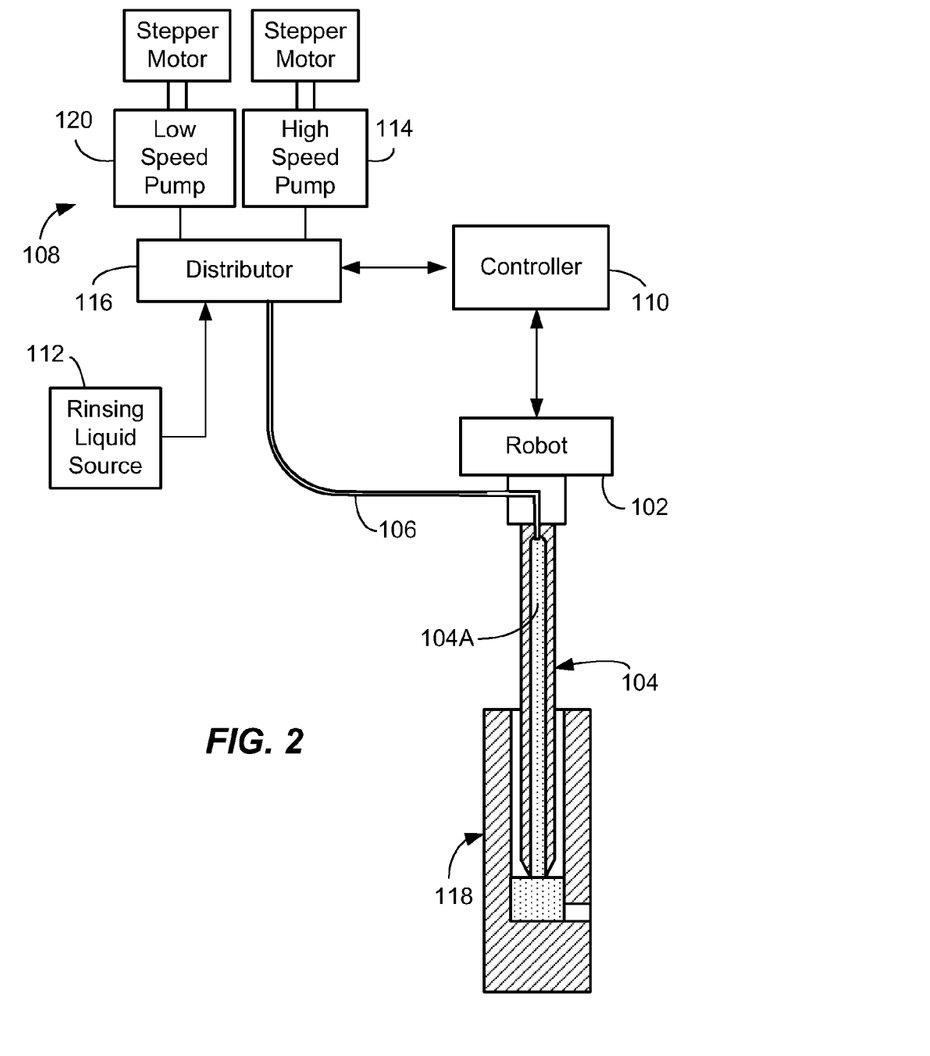
FIG. 2 is a partially cross-sectioned side view of an exemplary aspiration and dispensing system undergoing a rinse operation.

The aspirator/dispenser unit 108 may include any configuration adapted to aspirate and dispense fluids (liquids and gases). The aspirator/dispenser unit 108 may include one or more pumps, distributors, valves, filters, or other fluid-conveying components. For example, the aspirator/dispenser unit 108 may include two pumps as shown in FIG. 2. A high speed pump 114 may be coupled to a rinsing liquid source 112 by a distributor 116 such that a rinsing liquid from the rinsing liquid source 112 (e.g., a container or reservoir of purified water) may be provided in the tubing 106 and probe 104 to flush any sample and/or reagent remaining in the probe interior 104A from a previous dispense sequence.

During a conventional rinsing sequence, the rinsing liquid (e.g., purified water) may be dispensed from the interior 104A of the probe 104 to a drain station 118 as shown in FIG. 2 by the use of the high speed pump 114. In operation, a low speed pump 120 may be used for carefully metering and dispensing reagent 122 from the reagent container 124 (See FIG. 1) and/or biological fluid sample 123 from a sample container 125 (See FIG. 1) to a reaction vessel 127 to provide a combination 135 of reagent 122 and/or biological fluid sample 123. The pumps 114, 120 may be operated and driven by utilizing stepper motors.

Figure 3:
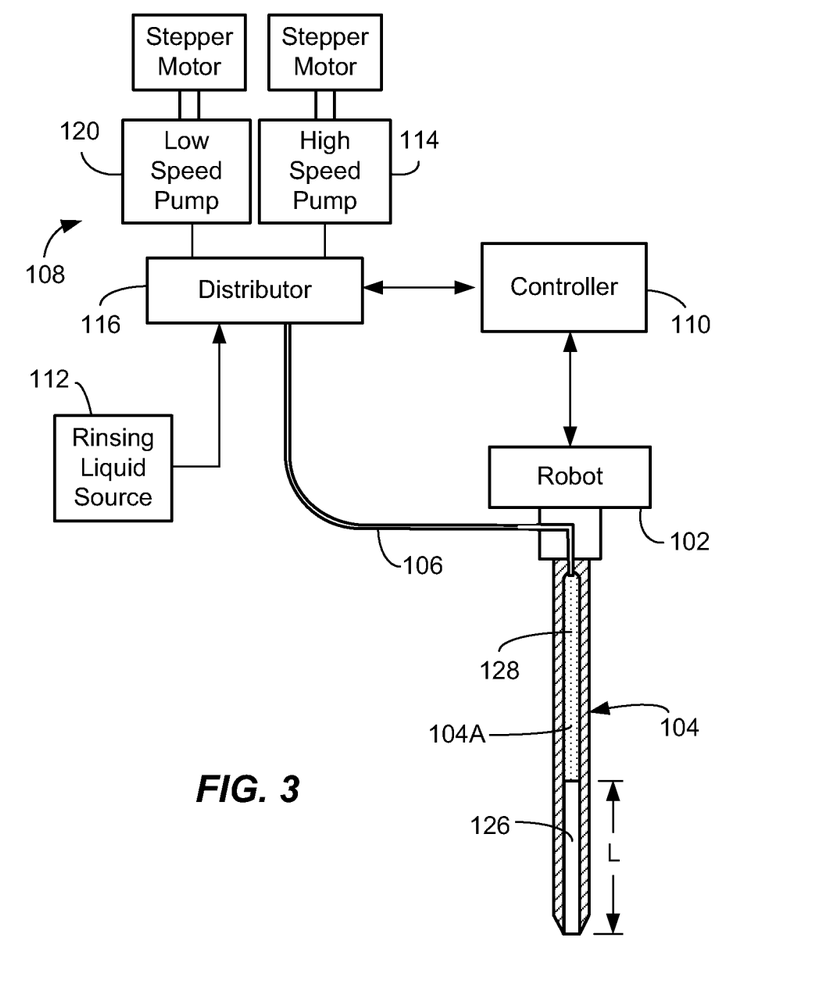
FIG. 3 is a partially cross-sectioned side view of an exemplary aspiration and dispensing system aspirating a gas slug into the probe according to an aspect of the invention.

In more detail, the inventive mixing method may start after flushing (as described above) or otherwise initially priming by providing the rinsing liquid (e.g., purified water) into the length of tube 106 and probe 104. With the probe 104 filled (primed) with rinsing liquid 128 initially, as shown in FIG. 1, the aspirator/dispenser unit 108 is operated to aspirate a gas slug 126 (e.g., an air slug) acting as an air separator into the probe interior 104A of the probe 104 as shown in FIG. 3. The gas slug 126 includes a length L that is less than the length of the interior 104A of the probe 104. The length may be between about 32 mm and about 87 mm. The volume of the gas slug 126 may be between about 12 µL and about 108 µL. The aspiration of the gas slug 126 may be carried out by the high speed pump 114. At this point in the method, the interior 104A of the probe 104 includes the gas slug 126 in a bottom interior portion and a volume of rinsing liquid 128 (e.g., purified water) at a top interior portion thereof.

Figure 4:
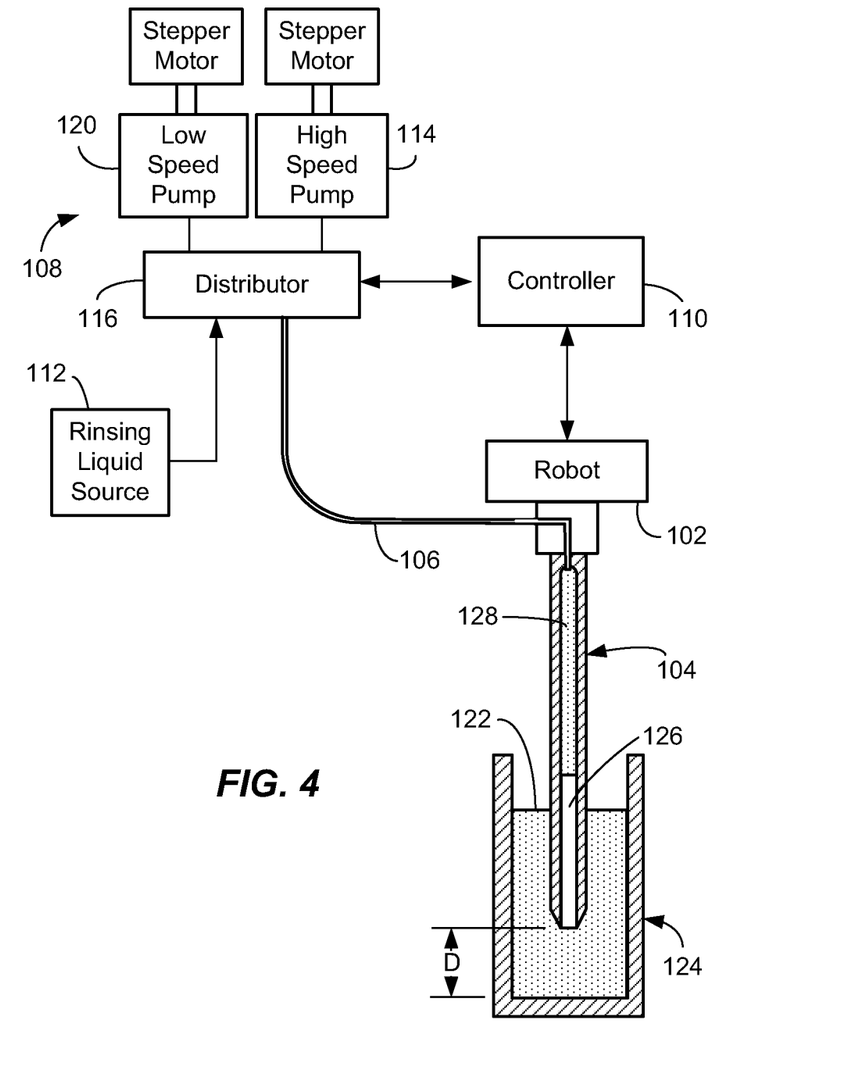
FIG. 4 is a partially cross-sectioned side view of an exemplary aspiration and dispensing system plunged into a reagent container according to an aspect of the invention.

Next, the probe 104 is inserted into the reagent container 124 to a predetermined depth as shown in FIG. 4 to accomplish mixing. The depth may be very near the bottom of the reagent container 124. Distance (D) may be between about 4 mm and 5 mm from the bottom. Other depths may be used. The aspirator/dispenser unit 108 now aspirates reagent 122 from a reagent container 124 into the interior 104A of the probe 104. The volume of reagent that is aspirated (also referred to as a reagent slug 130, FIG. 5) by the aspirator/dispenser unit 108 may be small enough such that the reagent slug 130 is contained solely within the interior 104A of the probe 104. In other words, the reagent slug 130 is never aspirated far enough to reach the tubing 106, so the reagent 122 never contacts the tubing 106. Thus, no reagent wetting of the tubing 106 may occur according to one possible advantage of the invention.

Figure 5:
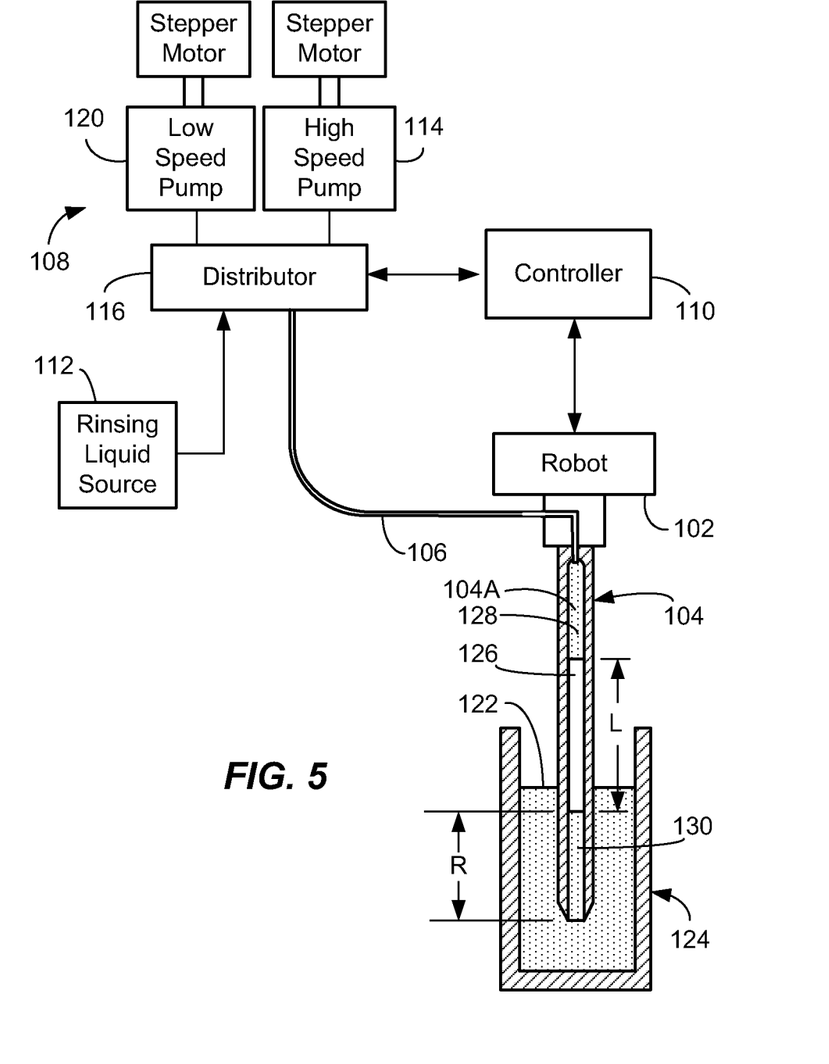
FIG. 5 is a partially cross-sectioned side view of an exemplary aspiration and dispensing system aspirating a reagent slug according to an aspect of the invention.
Figures 6A, 6B:
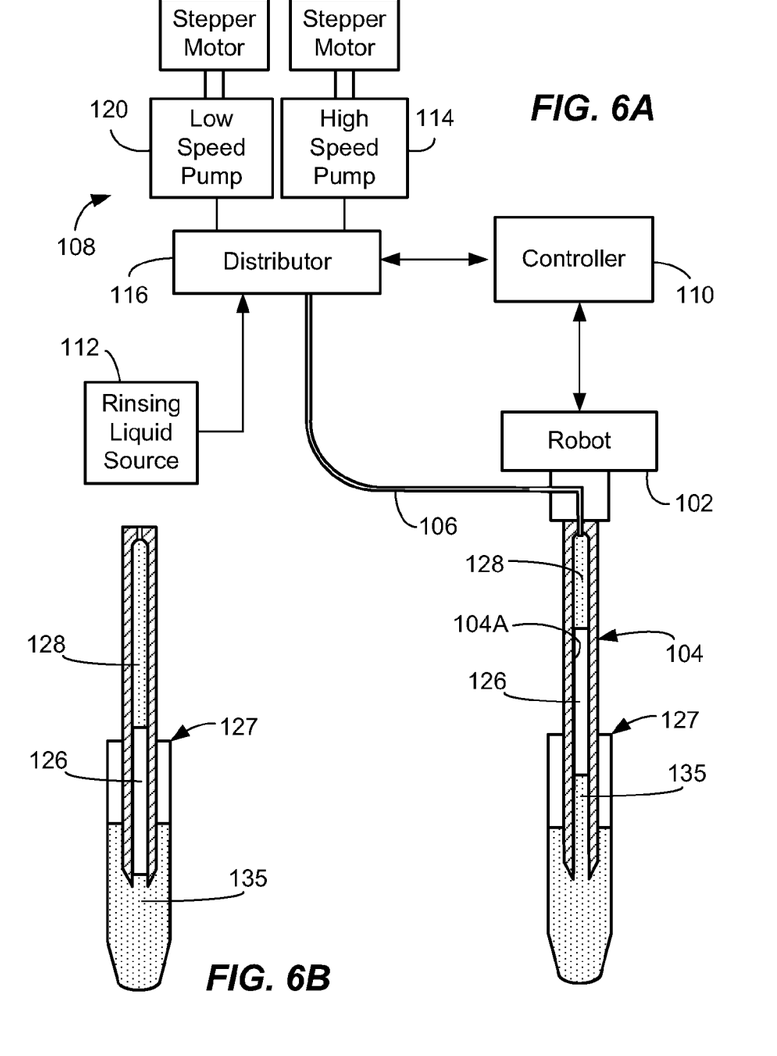
FIG. 6A is a partially cross-sectioned side view of an exemplary aspiration and dispensing system aspirating a combination of reagent slug and biological fluid sample according to an aspect of the invention.
FIG. 6B is a partial cross-sectioned side view of a probe of an exemplary aspiration and dispensing system dispensing a combination of reagent slug and biological fluid sample according to an aspect of the invention.

As shown in FIG. 5, the length (R) of the reagent slug 130 may be less than a length (L) of the gas slug 126. In some embodiments, the gas slug 126 is greater than about 1.2 times the length (R) of the reagent slug 130. Once the reagent slug 130 is aspirated, it is immediately dispensed back into the reagent container 124 to accomplish mixing of the reagent liquid 122. Following this, and without lifting the probe 104 out of the reagent fluid 122, another reagent slug 130 is again aspirated into the interior of the probe 104 in the same manner as shown in FIG. 5. This process of aspirating a short reagent slug 130 followed by re-dispensing the reagent slug 130 back into the container 124 is carried out in rapid succession. For example, the aspirating and dispensing may be accomplished at a frequency of greater than about 1 cycle/sec, or even at a frequency greater than about 3 cycles/sec. In some embodiments, the frequency of aspiration may be between about 2 cycles/sec and about 8 cycles/sec. Other frequencies greater than about 1 cycle/sec may be used.

It will be understood by those skilled in the art that, as compared to the volume of reagent aspirated via conventional sip-and-spit mixing methods, because the reagent slug 130 of the present invention is never aspirated far enough into the probe 104 so as to contact the tubing 106, the volume of the reagent slug 130 per each cycle of the present invention is substantially smaller than the volume of reagent aspirated per cycle in conventional methods wherein only one mixing cycle was used in the prior art method. A further unique feature of the present invention is the frequency (i.e., the number of repetitions in a unit of time) with which the aspirator/dispenser unit 108 operates (e.g., a high speed pump 114 such as a piston pump). In accordance with an aspect of the invention, during the mixing method, the aspirator/dispenser unit 108 operates to aspirate and dispense for at least 2 cycles, for at least 5 cycles, for at least 10 cycles, and in some embodiments for even at least 20 cycles or more. In some embodiments, about 25 cycles of aspirating and dispensing of the reagent slug 130 in rapid succession are accomplished. During the aspirating and dispensing of the reagent slug 130 in rapid succession, the probe preferably remains submerged in the liquid reagent 122. A cycle as used herein is composed of an aspiration and a dispensing of a single reagent slug 130. The volume of each newly-aspirated reagent slug 130 is approximately the same as the previously-aspirated reagent slug 130. The volume of each reagent slug 130 aspirated and then dispensed per cycle may be greater than about 10 μL, greater than about 20 μL, or even greater than about 25 μL, but less than the total interior volume of the probe 104. Other volumes, such as between about 10 μL and about 90 μL, or even between about 25 μL and about 75 μL may be cycled.

As explained above, conventional sip-and-spit methods employ a relatively low speed metering pump (and thus, relatively low fluid flow) during aspiration/dispensing of a relatively large volume of reagent to help ensure that the reagent remains intact during aspiration. It has been discovered that, by aspirating a smaller volume of reagent (i.e., a small reagent slug 130), and operating at a greater frequency, the mixing process may be enhanced. In general terms, the frequency (speed) at which the aspirator/dispenser unit 108 aspirates (sometimes measured in steps/second of the stepper motor) in the present mixing method may be approximately twice or more times the speed at which the aspirator/dispenser unit 108 may aspirate in conventional sip-and-spit mixing methods. Thus, the fluid flow during aspiration (measured in microliters/second) according the present mixing method may be approximately twice the fluid flow during aspiration in conventional mixing methods. For example, the aspiration rate may be greater than about 150 μL/sec.

For example, conventional mixing methods may operate the aspirator/dispenser unit 108 with an 800 steps/second aspiration speed and a 1600 steps/second dispense speed, resulting in a fluid flow of approximately 406 microliters/second during aspiration and 812 microliters/second during dispensing. In contrast, the mixing method of the present invention may operate the aspirator/dispenser unit 108 with 1600 steps/second aspiration speed and 1600 steps/second dispensing speed, resulting in a fluid flow of approximately 812 microliters/second during both aspiration and dispensing. These values are exemplary in nature, and the present invention is in no way limited to such speeds. It will be understood by those skilled in the art that the increased speed and frequency with which the aspirator/dispenser unit 108 may operate results in a more robust mixing operation of the reagent 122 in the reagent container 124.

Some particular advantages of the improved mixing method of the present invention include:

(1) particle reagents within compartments of reagent containers 124 may not be appreciably damaged, (2) reagent dilution due to water wetting within the tube 106 may be reduced or eliminated, thereby resulting in an improved dilution factor, (3) reagent wetting of the tube 106, and thus reagent lost due to reagent wetting within the tube, is substantially reduced or eliminated, (4) reagent carryover may be reduced or eliminated as reagent is contained only within the probe 104, (5) improved mixing forces may be provided and, thus, improved mixing of the reagent 122 in the container 124 may be provided, and (6) breaking up of aggregates in the reagent 122 may be improved at the tip of the probe 104 because of favorable shear force provided at the probe tip. Other advantages may be apparent.

The exemplary probe 104 for use with the present mixing method invention may be made from stainless steel with a titanium tip. The probe 104, however, is not limited to such materials, and may be constructed from aluminum or any other metal, composite material, or combination of materials. The probe may include an inner diameter between about 0.5 mm and about 1.4 mm. The exemplary tube 106 for use with the present mixing method invention may be made from polyethylene, and has an internal diameter of about 1.5 mm. The tube 106, however, is not limited to polyethylene, and may be constructed from any other polymer, metal, or any other material.

Figure 7:
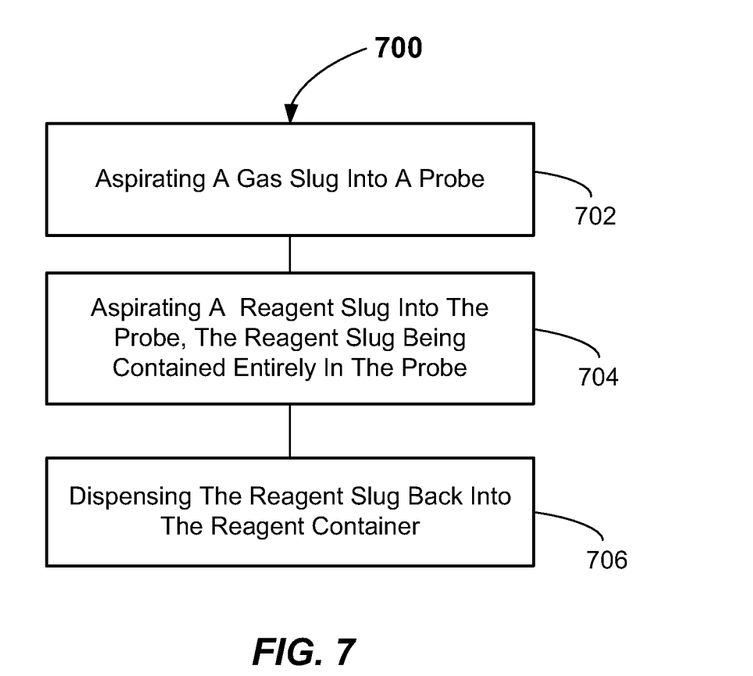
FIG. 7 is a flowchart illustrating a method according to embodiments of the present invention.

FIG. 7 describes a method of providing a liquid reagent in an automated clinical analyzer according to a broad aspect of the invention. The method includes aspirating a gas slug 126 into a probe 104 in 702; aspirating a reagent slug 130 into the probe 104 from a reagent container 124 in 704, the reagent slug 130 being contained entirely within the probe 104; and dispensing the reagent slug 130 back into the reagent container 124 in 706.

Figure 8:
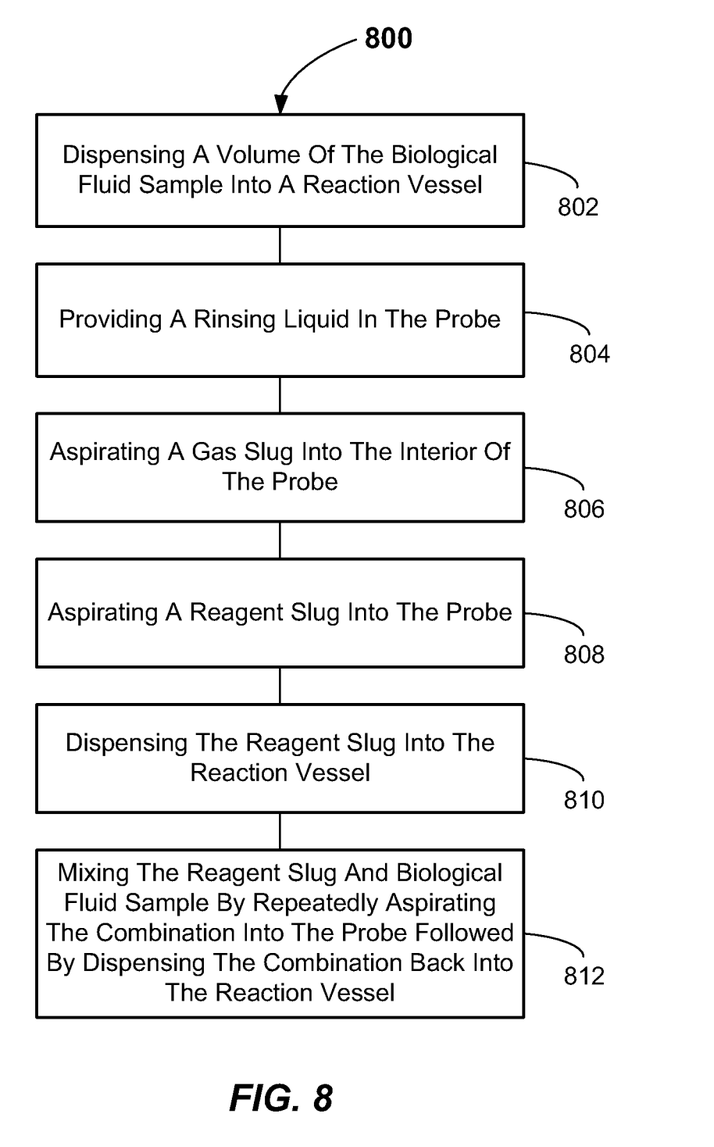
FIG. 8 is a flowchart illustrating another method according to embodiments of the present invention.

FIG. 8 illustrates a method of mixing a biological fluid sample in an automated clinical analyzer. The method 800 includes dispensing a volume of the biological fluid sample 123 into a reaction vessel 127 (e.g., cuvette) in 802. The dispensing of the biological fluid sample 123 into a reaction vessel 127 may be accomplished by the probe 104 shown or by a different probe. If the illustrated probe 104 is used, then the dispensing of the biological fluid sample 123 into a reaction vessel 127 may be followed by rinsing that may include dispensing a rinsing liquid from the probe 104 into a drain station 118. The rinsing may be preceded by exposure of the probe 104 to other cleaning fluids, together with showering and/or air knife cleaning of the outer surface of the probe 104. After the rinsing, if used, the interior 104A of the probe 104 is provided in 804 with a volume of rinsing liquid 128 that entirely fills the internal volume of the probe 104 as shown in FIG. 1. This rinsing liquid 128 may be provided by the rinsing liquid source 112 via operation of the aspirator/dispenser unit 108 dispensing a small amount of liquid to the drain station 118, and effectively priming the tube 106 and probe 104 with rinsing liquid 128 as shown in FIG. 2. Following this, a gas slug 126 is aspirated into the interior 104A of the probe 104 in 806 via aspiration action of the aspirator/dispenser unit 108 (e.g., by operating the stepper motor in reverse) as shown in FIG. 3. The gas slug 126 may have a volume of between about 12 μL and about 108 μL, for example. Other volumes may be used. As can be seen in FIG. 5, during the aspirating of the reagent slug 130 and the gas slug 126, a volume of rinsing fluid 128 is contained in the interior of the probe 104.

The probe 104 is inserted into the reagent container 124 to a point near the bottom thereof as shown in FIG. 4. Next, a reagent slug 130 is aspirated into the interior 104A of the probe 104 in 808 as shown in FIG. 5 by the aspiration action of the aspirator/dispenser unit 108, wherein the reagent slug 130 is separated from a volume of rinsing liquid 128 by the gas slug 126. The reagent slug 130 may have a volume of above about 10 μL but less than the interior volume of the probe 104. In some embodiments, the reagent slug 130 may have a volume of between about 10 μL and about 90 μL, or even between about 25 μL and about 75 μL. Other volumes may be used that are less than the interior volume of the probe 104. Typically, the gas slug 126 may have a volume of about 1.2 or more times larger than the reagent slug 130.

Next, in 810, the probe 104 is repositioned over the reaction vessel 127, lowered to at least the surface of the sample contained therein, and the reagent slug 130 is dispensed into the reaction vessel 127 along with the biological fluid sample previously dispensed into the reaction vessel 127. The order of dispensing of the reagent slug 130 and the biological fluid sample can be reversed. In 812, the combination 135 of dispensed reagent slug and dispensed biological fluid sample are mixed by repeatedly aspirating the combination 135 of reagent slug and biological fluid into the interior 104A of the probe 104 followed by dispensing the combination 135 back into the reaction vessel 127. In some embodiments, the aspiration and dispensing of the combination 135 may be at a rate greater than about 1 cycle/sec. The aspiration and dispensing of the combination may be repeated for greater than 2 cycles and, in some embodiments, between about 2 cycles and about 10 cycles, or about 5 cycles to accomplish thorough mixing of the combination. During the cycling, the probe 104 remains submersed in the combination 135. A small slug of combined fluid 135 is repeatedly aspirated (FIG. 6A) and re-dispensed (FIG. 6B) into the reaction vessel 127 to accomplish improved mixing of the sample and the reagent. The volume of each slug of combined fluid 135 is approximately the same.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A method of providing a liquid reagent in an automated clinical analyzer, the method, comprising:
   aspirating a gas slug into a probe;
   aspirating a reagent slug into the probe from a reagent container, the reagent slug being contained entirely within an interior of the probe; and
   dispensing the reagent slug back into the reagent container wherein a length (R) of the reagent slug is less than a length (L) of the gas slug,
   wherein a volume of the reagent slug is greater than about 10 μL but less than an interior volume of the probe.

2. The method of claim 1, comprising operating an aspirator/dispenser unit fluidly coupled to the probe at an aspiration rate of greater than about 150 μL/sec.

3. The method of claim 1, wherein the aspirating of the reagent slug into the probe from the reagent container and the dispensing of the reagent slug back into the reagent container is performed at a frequency greater than about 1 cycle/sec, wherein one cycle includes both the aspirating and the dispensing.

4. The method of claim 3, wherein the cycling is at a frequency greater than about 3 cycles/sec.

5. The method of claim 3, wherein the cycling is at a frequency of between about 2 cycles/sec and about 8 cycles/sec.

6. The method of claim 1, wherein during the aspirating of the reagent slug and aspirating of the gas slug, a volume of rinsing fluid is contained in the interior of the probe.

7. The method of claim 1, further comprising, after mixing by repeatedly aspirating a reagent slug into the probe from the reagent container and dispensing a reagent slug back into the reagent container, aspirating a reagent slug and dispensing the reagent slug into a reaction vessel containing a biological fluid sample.

8. The method of claim 1, further comprising aspirating a reagent slug and dispensing the reagent slug into a reaction vessel containing a biological fluid sample, followed by cycling a combination of reagent and biological fluid sample into and out of the probe to accomplish further mixing of the combination in the reaction vessel.

9. The method of claim 1, further comprising coupling an aspirator/dispenser to the probe by a length of tubing, wherein only rinsing fluid is contained in the tubing.

10. The method of claim 1, further comprising mixing the reagent in the reagent container by dispensing and re-aspirating reagent slugs for at least 2 cycles.

11. The method of claim 1, further comprising mixing the reagent in the reagent container by dispensing and re-aspirating reagent slugs for at least 10 cycles.

12. The method of claim 1, further comprising mixing the reagent in the reagent container by dispensing and re-aspirating reagent slugs for at least 20 cycles.

13. The method of claim 1, further comprising, without moving the probe from the reagent container, re-aspirating another reagent slug into the probe.

14. The method of claim 1, wherein after aspirating the gas slug into the probe and aspirating the reagent slug into the probe, the probe includes the gas slug, the reagent slug, and a volume of rinsing liquid, wherein the gas slug is contained between the reagent slug and the volume of rinsing liquid.

15. A method of mixing a biological fluid sample in an automated clinical analyzer, the method, comprising:
   dispensing a volume of the biological fluid sample into a reaction vessel;
   providing a rinsing liquid in a probe;
   aspirating a gas slug into the probe;
   aspirating a reagent slug into the probe, wherein the reagent slug is separated from the volume of rinsing liquid by the gas slug, wherein the gas slug has a volume of about 1.2 or more times larger than a volume of the reagent slug, and the volume of the reagent slug is greater than about 10 μL but less than an interior volume of the probe;

dispensing the reagent slug into the reaction vessel along with the biological fluid sample; and mixing a combination of reagent slug and biological fluid sample by repeatedly aspirating the combination into the probe followed by dispensing the combination back into the reaction vessel.

16. The method of claim 1, comprising operating an aspirator/dispenser unit fluidly coupled to the probe at an aspiration rate of greater than about 150 μL/sec, and cycling is at a frequency of between about 2 cycles/sec and about 8 cycles/sec, wherein one cycle includes both the aspirating and the dispensing of the reagent slug.

\* \* \* \* \*